United States Patent [19]
Wilson

[11] Patent Number: 5,746,313
[45] Date of Patent: May 5, 1998

[54] MIXING CAPSULE AND METHOD OF MANUFACTURING SAME

[75] Inventor: Michael S. Wilson, Minden, Nev.

[73] Assignee: Wykle Research, Inc., Carson City, Nev.

[21] Appl. No.: 695,629

[22] Filed: Aug. 12, 1996

[51] Int. Cl.[6] .................................................. B65D 25/08
[52] U.S. Cl. .............................. 206/220; 206/221; 215/355
[58] Field of Search .................................. 206/219, 220, 206/221; 215/DIG. 8, 355; 366/602

[56] References Cited

U.S. PATENT DOCUMENTS

| | | |
|---|---|---|
| 3,785,481 | 1/1974 | Allet-Coche . |
| 3,796,303 | 3/1974 | Allet-Coche . |
| 3,860,114 | 1/1975 | Merckardt . |
| 3,900,122 | 8/1975 | Dichter .................. 215/355 |
| 3,902,477 | 9/1975 | Gerarde .................. 215/355 |
| 3,909,225 | 9/1975 | Rooney . |
| 4,182,447 | 1/1980 | Kay . |
| 4,188,457 | 2/1980 | Throp .................... 215/355 |
| 4,197,943 | 4/1980 | Weikel . |
| 4,227,620 | 10/1980 | Conway .................. 215/355 |
| 4,362,242 | 12/1982 | Cheetham . |
| 4,433,779 | 2/1984 | Schmid, Jr. et al. . |
| 4,449,645 | 5/1984 | Korwin et al. . |
| 4,515,267 | 5/1985 | Welsh . |
| 4,526,472 | 7/1985 | Zaltsman . |
| 4,863,017 | 9/1989 | Vlock . |
| 4,966,465 | 10/1990 | Randklev . |
| 5,335,773 | 8/1994 | Haber et al. . |
| 5,344,036 | 9/1994 | Stanescu et al. ........ 215/355 |
| 5,392,904 | 2/1995 | Frick et al. . |
| 5,394,980 | 3/1995 | Tsai . |

*Primary Examiner*—Paul T. Sewell
*Assistant Examiner*—Nhan T. Lam
*Attorney, Agent, or Firm*—Fulwider Patton Lee & Utecht, LLP

[57] ABSTRACT

A dental amalgam mixing capsule including an inner capsule housed in an outer capsule. The inner capsule includes an elongated pestle telescopically extended into an open ended cap including a resilient, annular skirt formed with an annular sealing lip sized for frictional, gripping engagement with the pestle to define a storage chamber therebetween for storing a liquid component of the amalgam. The inner capsule may be made by subjecting the cap to a partial vacuum, inserting a charge of such liquid component therein, and registering one end of such pestle in sealing engagement with such sealing lip. Thus, when the assembly is returned to atmospheric pressure, the partial vacuum trapped in the cap will provide for a pressure differential across the pestle drawing it into the cap to fill the space therein.

25 Claims, 4 Drawing Sheets

MIXING CAPSULE AND METHOD OF MANUFACTURING SAME

BACKGROUND OF THE INVENTION

1. Field of the Invention

The present invention relates to a compact storage device for storing a pair of ingredients which in combination form a composition and, more particularly, to a device for storing such ingredients separated from one another and providing a means for conveniently and efficiently mixing such ingredients into a composition for use.

2. Description of the Prior Art

Dental amalgams are frequently used by dentists to fill in cavities drilled in a patient's teeth. Such amalgams typically comprise a combination of an alloy powder and an amount of liquid mercury. The alloy typically consist of gold or silver combined with copper, zinc and tin. It is well known that the composition of alloy powder and liquid mercury, immediately after the two ingredients are mixed, temporarily forms a pliable composition which may be manipulated and deformed, and then quickly forms a hardened, solid composition. Thus, such compositions are ideal to serve as fillings where the shape of the cavity will vary depending on the extent of decay of the tooth. After drilling to remove the decayed material, the dentist may mix the ingredients and insert the pliable amalgam into the cavity to fill the entire cavity. The amalgam then quickly hardens in the surrounding tooth material to effectively replace the removed material and will be sufficiently durable to withstand the forces exerted thereupon by the patient from activities such as chewing and the like.

Due to the above-mentioned properties of such dental amalgams, namely initially being soft and pliable but then quickly hardening to form a solid, non-pliable mass, the ingredients must be stored separately until just prior to the time the dentist requires the amalgam in order to fill a cavity. Any premature mixing of the ingredients results in an unusable composition which hardens before it is needed and thus must be discarded.

A number of prior art storage and mixing capsules have been provided which are formed with a pair of chambers for storing discrete ingredients and separated by a rupturable partition. When the amalgam is needed, the partition is ruptured to allow the two ingredients to come together and mix to form the amalgam. Forms of such apparatus are disclosed in U.S. Pat. Nos. 3,860,114, 4,182,447 and 5,394,980. Such apparatus are not free from shortcomings, however. In the first place, such apparatus are not readily reusable. Once the partition is ruptured, the capsule is no longer compartmentalized and thus is no longer suitable for separately storing two ingredients. In addition, such apparatus are relatively expensive to manufacture with the rupturable partition often being formed integrally with a portion of the mixing capsule. Thus, in order to reuse such mixing capsules, the mixing capsule will require a tedious and inefficient remanufacture.

There have also been proposed dental mixing capsules which include movable pistons or the like which are movable relative to the capsule to expose an internal passageway to allow previously separated ingredients to mix to form the amalgam. A form of such apparatus is shown in U.S. Pat. No. 4,449,645. While satisfactory generally, such apparatus are somewhat expensive to manufacture as they require a relatively detailed internal configuration. In addition, if during transport the piston is accidentally struck, the internal passageway will potentially be exposed resulting in a premature mixing of the ingredients and thus an unusable composition.

Another device proposed in effort to solve the above-described problems is disclosed in U.S. Pat. No. 4,197,943 to Weikel, and assigned to the assignee of the rights in the instant invention. The device exhibits excellent operational characteristics. However, the device requires a relatively large number of machined or molded parts and is thus somewhat expensive to manufacture.

Yet another proposed device is disclosed in U.S. Pat. No. 4,526,472 to Zaltsman. The device comprises an outer capsule and inner capsule, the inner capsule including a pair of open-ended cap members frictionally engaged with one another. The respective members are formed with a complemental stem and bore configuration, the stem being slidable within the bore and normally sealing the bore to trap an amalgam ingredient within the inner capsule. When the inner capsule is impacted against an inner face of the outer capsule during vibration of the device, the stem is purportedly driven relative to the bore to open a passageway therethrough to allow the ingredient to flow into the outer capsule to mix with the ingredient stored therein. This device, however, requires that the two members be particularly formed in order to provide the complemental stem and bore arrangement. Additionally, the stem is relatively small in cross-sectional dimension and yet must come into direct contact with the inner face of the outer capsule in order to open the passageway through the bore. Thus, in order to perform properly, the device requires that the inner capsule follow a precise travel path during vibration of the device.

As such, it will be appreciated that there continues to be a need for a simple and efficient mixing capsule assembly to separately store the ingredients of a dental amalgam and to conveniently and reliably mix such ingredients when desired to create the amalgam. In addition, there continues to be a need for such a device which incorporates a relatively small number of relatively inexpensive components and which is thus easy and efficient to assemble. The present invention addresses these needs and others as described in greater detail hereinbelow.

SUMMARY OF THE INVENTION

The present invention provides an efficient, inexpensive, easy to use dental amalgam mixing capsule for separately storing a pair of ingredients therein and providing means for, when desired, efficiently and reliably mixing such ingredients to form the amalgam.

Briefly, and in general terms, the mixing capsule of the present invention includes an inner storage capsule apparatus to be housed within an outer capsule defining an interior mixing chamber therewithin. The inner capsule comprises an elongated, generally cylindrical pestle and a cap configured with a cavity for storing a liquid component of the amalgam therein and including and open end for telescopically receiving one longitudinal end of the pestle. The cap is formed with a deflectable, resilient annular skirt terminating at the open end of the cap in a radially inwardly extending annular sealing lip sized for frictionally engaging the peripheral wall of the pestle to trap the liquid component in the chamber defined by the cap and pestle. When the mixing capsule assembly is subjected to a vibration movement, driving such inner capsule in opposite axial directions, the cap will impact the inner wall of the outer capsule thus abruptly decelerating such cap so that the high velocity of the pestle will cause the momentum of such pestle to drive it a measured distance into such cavity and against the liquid component stored therein to generate a sufficient hydraulic pressure to stretch the annular skirt allowing it to be lifted radially outwardly to lift the sealing lip up off the peripheral wall of the pestle to allow a measured quantity of the liquid component to escape the inner capsule and enter the mixing chamber to mix with the ingredient stored therein to form the dental amalgam.

Other features and advantages of the present invention will become apparent from the following detailed description, taken in conjunction with the accompany drawings which illustrate, by way of example, the features of the invention.

DETAILED DESCRIPTION OF THE PREFERRED EMBODIMENT

Figure 1:
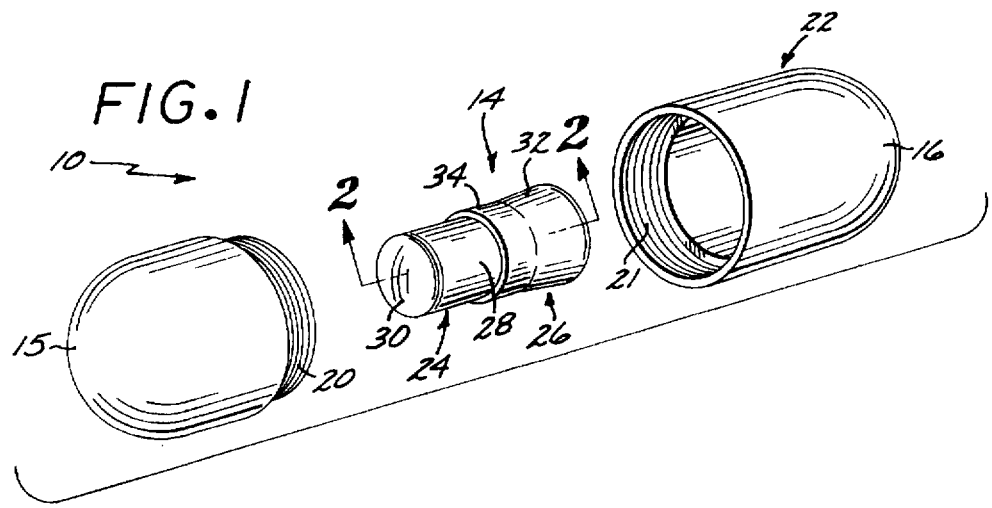
FIG. 1 is an exploded perspective view of an outer capsule and an inner capsule embodying the present invention.

In the following detailed description, like reference numerals will be used to refer to like or corresponding elements in the different figures of the drawings. Referring now to the drawings, and particularly to FIG. 1, there is shown, generally, a dental amalgam mixing capsule assembly 10, including an outer capsule 12 and an inner capsule 14. The mixing capsule assembly of the present invention provides an economical, reliable storage and mixing assembly that incorporates a relatively small number of components while at the same time assures that no accidental mixing of the two ingredients will occur such as during transport thereof from the manufacturing site to the dentist's office.

Figures 3, 4:
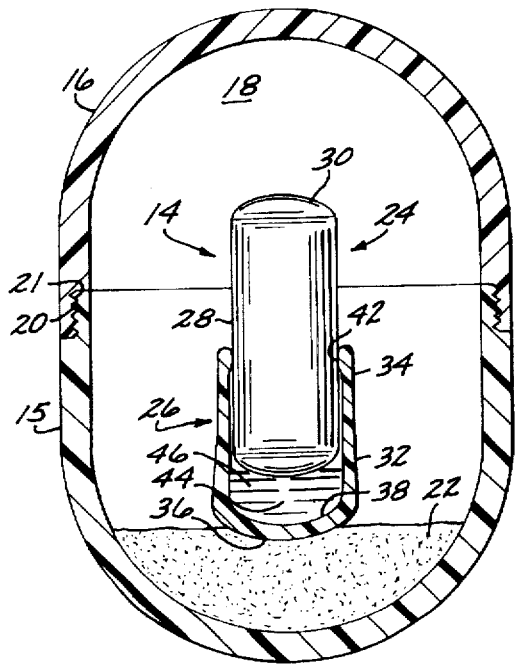
FIG. 3 is a sectional view, in enlarged scale, of the inner capsule housed in the sealed outer capsule shown in FIG. 1 prior to subjecting the assembly to a vibration movement.
FIG. 4 is a cross-sectional view similar to FIG. 3 but showing the assembly subsequent to subjecting same to a vibration movement.

The outer capsule 12 comprises a pair of generally cylindrical, opposing, open-ended end caps 15 and 16 releasably engageable to each other to form the sealed outer capsule and define an interior mixing chamber 18 therewithin (FIGS. 1, 3 and 4). The cap 15 is formed on its open end with a reduced in diameter neck projection 20 which may be externally threaded. The mating cap 16 is formed at its open end with an internally threaded region 21 for threaded engagement with the externally threaded neck 20 formed on the first end cap 15. The outer capsule stores in the interior mixing chamber 18 a predetermined quantity of an alloy powder 22 comprising an ingredient of the dental amalgam 23. The alloy powder typically comprises either gold or silver mixed with copper, tin and zinc, as is well known in the art.

Figure 2:
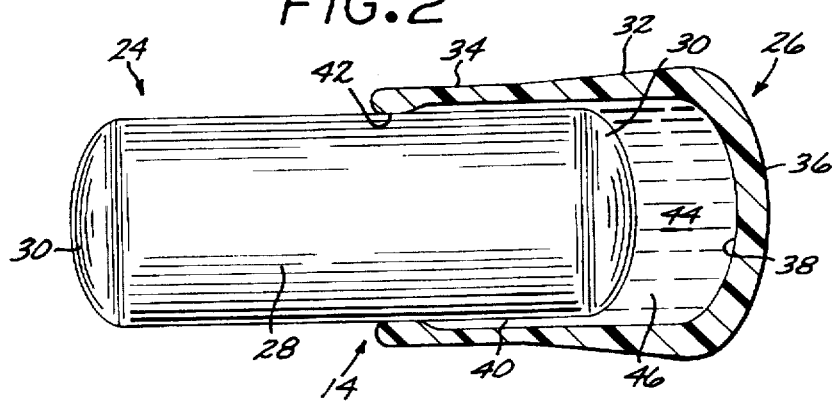
FIG. 2 is a cross-sectional view, in enlarged scale, taken along the line 2—2 of FIG. 1 showing the inner capsule.

Referring to FIGS. 1 and 2, the inner capsule 14 of the present invention is generally cylindrically shaped to form a longitudinal axis. Such inner capsule comprises an elongated, cylindrical pestle, generally designated 24, and an open ended, cylindrical storage cap device, generally designated 26. The pestle is preferably formed of a solid piece of plastic or other relatively dense material such as stainless steel to provide a sufficient mass to aid in the mixing of the ingredients as described in greater detail below. The central body portion 28 of the pestle is generally cylindrical in configuration and is capped at its opposite longitudinal ends by respective hemispherical end walls 30. In the exemplary embodiment shown the pestle is shown as cylindrical but, as will be apparent to those skilled in the art, it is only important that the pestle have a uniform cross-section throughout the length of its engagement with the cap 26. For convenience herein, that cross-sectional shape, whether it be square, oval, rectangular or any one of another of well known substitutes will be referred to as cylindrical.

The storage cap device 26 includes a generally cup-shaped hollow cap 32 formed with a closed end wall 36 and formed at its open end with a deflectable, resilient annular skirt 34 for complemental engagement with the side wall of the pestle 24. As such, the pestle may be telescopically extended into the storage cap to expel the air therein and cause the end wall 30 to abut against the interior wall 38 thus fully occupying the axial space of the cap cavity.

The inside diameter of the annular skirt 34 is formed having a slightly larger dimension than the cross-sectional diameter of the pestle 24. As such, an annular fluid passageway 40 is defined between the peripheral skirt and outer wall of the pestle.

The annular skirt 34 terminates at the open end of the storage cap 26 in a radially inwardly projecting sealing lip 42 sized for frictional, gripping engagement with the peripheral sealing wall of the pestle 24 (FIG. 2). The frictional, gripping engagement may be overcome by applying sufficient force in an axial direction to the pestle to allow the pestle to be moved relative to the storage cap. The pestle, storage cap and sealing lip cooperate to define a storage chamber 44 therebetween for storing a predetermined quantity of a liquid component 46 of the dental amalgam therein, such as liquid mercury.

The annular skirt 34 is formed of a flexible material such as plastic and is sized such that the sealing lip 42 normally makes a fluid-tight seal against the peripheral sealing wall of the pestle 24. The skirt is responsive to a pressure above a threshold level being applied to the interior thereof to be expanded radially outwardly to lift the sealing lip off the peripheral wall of the pestle to provide for a measured amount of the liquid component to be driven from the storage cap 26 and into the interior mixing chamber 18 of the outer capsule 12. When the pressure applied to the interior of the annular skirt falls below the threshold level, the inherent elasticity thereof will draw such skirt again into sealing engagement with the peripheral wall of the pestle to again seal the storage chamber 44.

It will be appreciated that the annular skirt 34 may be formed with sufficient resiliency to normally constrain the skirt 34 radially inwardly with sufficient force to maintain the sealing lip 42 on the peripheral wall of the pestle 24 with sufficient force to maintain the liquid component 46 sealed securely in the storage cap 26 to prevent premature escape thereof.

The outer capsule 12 and storage capsule 26 may be formed of a polymeric or thermoplastic material and may be formed using injection molding techniques well known to those skilled in the art. In addition, those materials have been selected to be chemically compatible with the components of the amalgam to be stored and mixed in the capsule.

Referring particularly to FIGS. 1, 2, 6 and 7, the preferred method of making the inner capsule 14 will now be described. To assemble the inner capsule, a worker may first retrieve a pestle 24, storage cap 26 and a supply of the liquid component 46. The storage cap is then positioned such that the open end thereof is facing generally upwardly and the desired charge of liquid component dispensed therein. The worker will then grasp the pestle and register one longitudinal end thereof with the open end of the cap. The pestle may then be telescopically driven manually under force into the cap expelling trapped air around the periphery of such pestle until the liquid component completely fills the internal storage chamber 44 defined by the cap, pestle and sealing lip 42.

Figure 7:
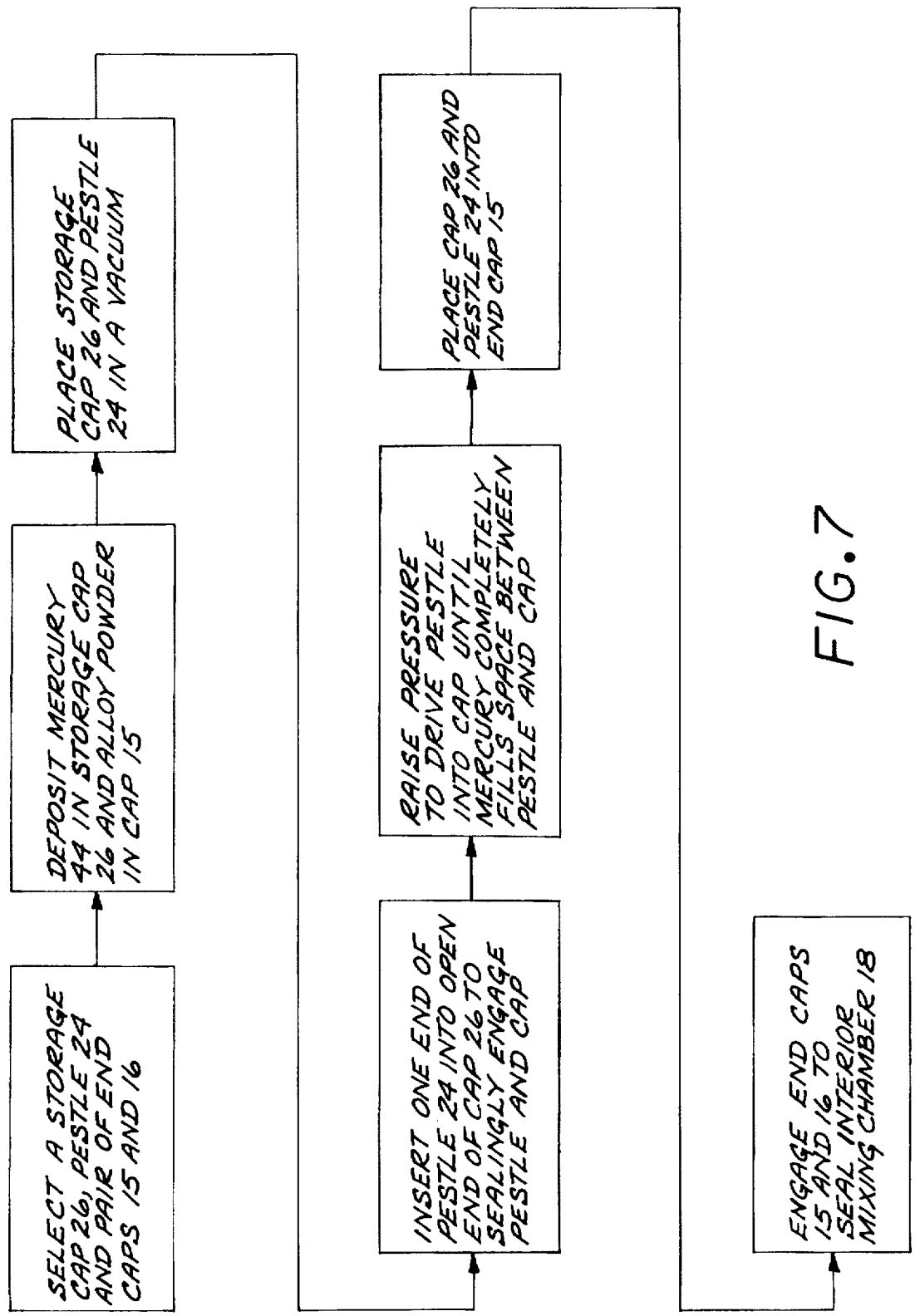
FIG. 7 is a schematic diagram illustrating a second embodiment of a method of making the capsule assembly of the present invention.

In the preferred embodiment, as shown diagrammatically in FIG. 7, the assembly of the inner capsule 14 may be performed in a vacuum chamber or the like to facilitate insertion of the pestle 24 into the storage cap 26. In this form of assembly the partial vacuum trapped in the cap when the pestle is registered in sealing engagement with the seal 42 to, when the external pressure is raised such as by removing the cap and pestle from the vacuum chamber or by venting the chamber, provide a pressure differential across the pestle causing such pestle to be driven axially into such cap to the degree dictated by the magnitude of the initial partial vacuum. It will be appreciated that the only resistance to such pestle being so driven into such cap will be the frictional engagement of the sealing lip 42 with the peripheral wall of the pestle until the liquid component completely fills the internal storage chamber 44. When this occurs, the partial vacuum is completely displaced by the liquid component which prevents the pestle from being further driven into the cap. The assembly of the inner capsule 14 is then complete, and the inner capsule is ready for packaging to be shipped to the customer dentist or other user's place of business.

It will also be appreciated that the pestle 24 could be formed with a circumferential indicator disposed at a predetermined position on the peripheral wall thereof to correspond with the proper degree of insertion of the pestle into the storage cap 26 so that, when the pestle is inserted into the cap to a sufficient extent that the indicator aligns with the open end of the storage cap, the storage chamber 44 is completely filled with the liquid component 46.

If the entire mixing capsule assembly 10 is to be assembled at the manufacturer's site, the worker may, after assembling the inner capsule 14, select a pair of engageable end caps 15 and 16 and a predetermined quantity of an alloy powder 22. The worker may take one of the caps and orient such cap so that the open end is facing generally upwardly and then deposit the quantity of alloy powder into such cap and place the assembled inner capsule 14 therein as well. The worker may then grasp the other end cap and orient such end cap so that the open end thereof opposes the open end of the end cap storing the alloy powder and inner capsule. The worker may then bring the respective end caps together so that the respective threaded regions 20 and 21 are engaged. The end caps are then rotated relative to one another until the respective threaded regions are completely engaged to form the outer capsule 12. As such, the interior mixing chamber 18 is completely sealed and the mixing capsule assembly 10 is then ready for storage or transport to the dentist's or other user's place of business.

It will thus be appreciated from the above description of the assembly process that the relatively small number of components utilized in the inner capsule 14 and in the entire mixing capsule assembly 10 facilitates efficient and convenient assembly of the inner capsule and of the mixing capsule assembly for completion in a minimal amount of time and with a minimum number of assembly steps.

Figure 5:
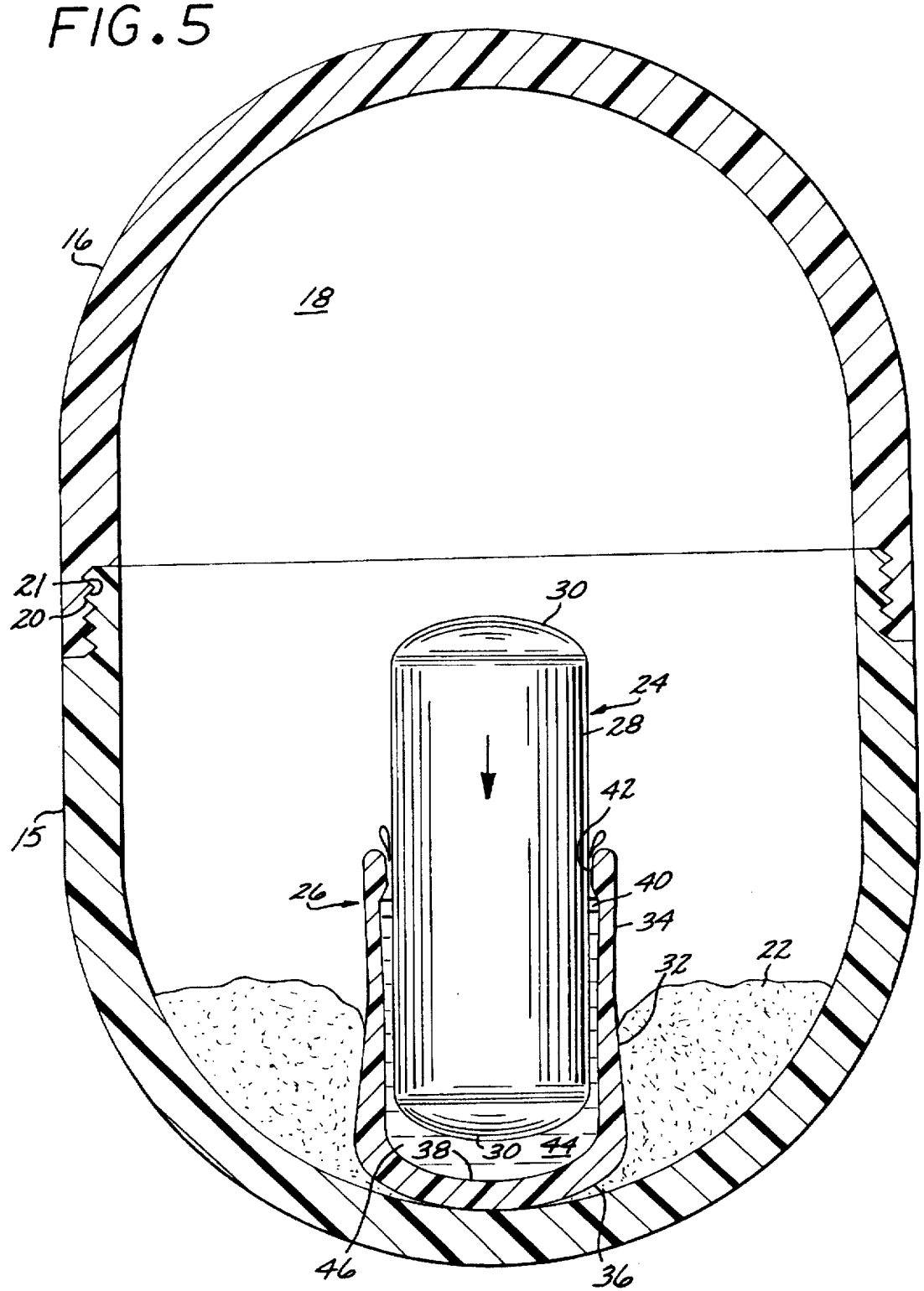
FIG. 5 is a cross-sectional view, in enlarged scale, and similar to FIG. 3 but showing the mixing capsule assembly during vibration thereof.
Figure 6:
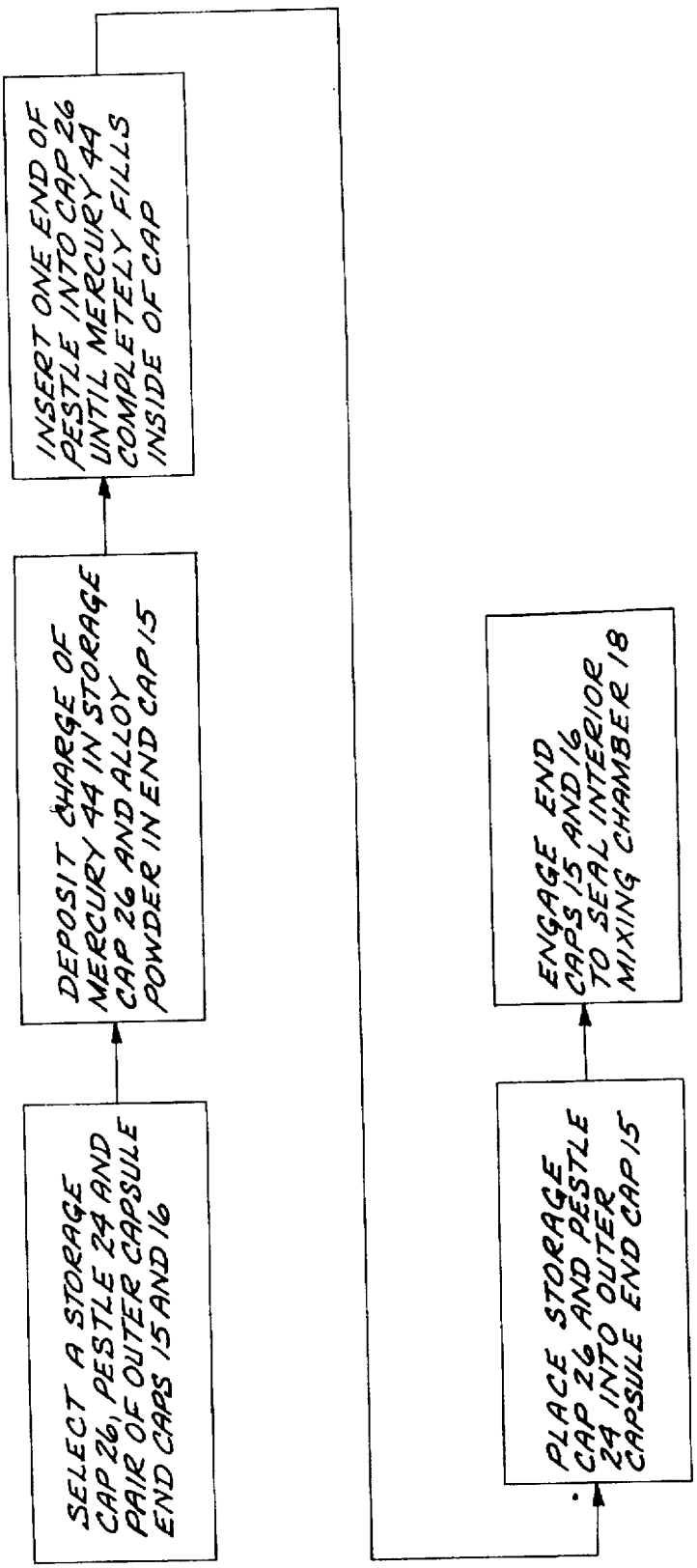
FIG. 6 is a schematic diagram illustrating an embodiment of a method of making the mixing capsule assembly of the present invention.

Referring now to FIGS. 3, 4 and 5, operation of the mixing capsule assembly 10 to form the dental amalgam will now be described in detail. To join the liquid component 46 and alloy powder 22 together for mixing thereof to form the amalgam, the user may retrieve the mixing capsule assembly 10 from storage and place the mixing capsule assembly in a conventional amalgamator or other type of mechanical vibrating device. The device is then actuated to subject the capsule to a vigorous vibratory movement, typically on the order of several thousand cycles per minute. As the mixing capsule assembly is vibrated, the inner capsule 14 will be alternately accelerated at different periods of time in opposite longitudinal directions within the outer capsule 12, thus repeatedly striking the opposite inner walls of the outer capsule. As shown in FIG. 5, as the storage cap 26 impacts axially against the inner surface of the wall of the outer capsule 12, the pestle 24 will have a tendency to, under its own momentum, continue moving toward the inner wall of the outer capsule, as indicated by the arrow in FIG. 5. As such, the pestle acts as a piston to, when accelerated to a high velocity, tend to continue movement in the direction of travel so that, when the cap strikes the inner end of the outer capsule 12 as shown in FIG. 5, such pestle will apply a relatively large force to the liquid component 46 stored in the storage chamber 44 to create a relatively large hydraulic pressure in the internal storage chamber 44. Such hydraulic pressure will force the mixture 44 up the annular passage 40 to exert radially outward pressure on the annular skirt 34 of sufficient magnitude to deflect the skirt radially outwardly to break the seal between the lip 42 and the peripheral wall of the pestle to thereby create a flow passageway for seepage of a controlled measure of liquid component from the storage chamber and into the mixing chamber 18. As the measure of liquid component is driven from the storage cap 26 the displaced volume thereof will afford further room for the pestle to be driven further into the cap. The controlled measure of liquid component will then be mixed with the alloy powder 22 to thereby achieve a progressive mixing action as such powder is also vibrated.

This process is repeated as the mixing capsule is continuously vibrated until the last of the liquid component is driven from the inner capsule and the pestle is driven through its complete travel path into the storage cap 26 to be disposed with its proximate end in abutting relationship with inner end wall of the storage cap as shown in FIG. 4. The capsule may then be further vibrated to continue mixing of the liquid component and alloy powder, with the inner capsule aiding in the process. After the mixing process is completed, which will typically be on the order of one to two minutes, the user may remove the mixing capsule 10 from the amalgamator and rotate the end caps 15 and 16 relative to one another to disengage such end caps and expose the interior mixing chamber 18. The dental amalgam may then be conveniently removed and applied to a cavity or cavities in a patient's tooth or teeth as needed.

It will be appreciated that the end caps 15 and 16, pestle 24 and storage cap 26 are all reusable and, as such, the mixing capsule assembly 10 provides an efficient, easy-to-use apparatus for preparing a dental amalgam. Because none of the component parts are ruptured or otherwise damaged during the mixing process, the above-described method of assembly may be repeated with the same parts by simply obtaining new quantities of the alloy powder and liquid component.

From the foregoing, it will be appreciated that the dental amalgam mixing capsule assembly 10 of the present invention provides a compact device for separately storing the pair of components of a dental amalgam therein and, when desired, for conveniently mixing such components to create the dental amalgam. In addition, the mixing capsule assembly incorporates a relatively small number of components such that assembly of the device is facilitated. Furthermore, such parts are all reusable, thus enhancing the efficiency of the device.

While a particular form of the present invention has been illustrated and described, it will be apparent that various modifications can be made without departing from the spirit and scope of the invention. Accordingly, it is not intended that the present invention be limited, except as by the appended claims.

What is claimed is:

1. A dental amalgam storage capsule device comprising:

an elongated pestle of a predetermined cross-sectional configuration to define an a barrel having an elongated peripheral sealing wall; and a cap formed with a mercury storage compartment and configured with a peripheral skirt defining an opening receiving said barrel, said skirt terminating in a resilient sealing lip having sufficient resiliency to, upon receipt of mercury in said compartment, normally seal against said sealing wall with sufficient force to normally maintain a tight seal against flow of said mercury and responsive to, upon insertion of said pestle into said compartment to contact said mercury and raise the hydraulic pressure thereof to a predetermined pressure, sealingly disengage said wall for flow of at least a portion of said mercury between said lip and wall.

2. The apparatus of claim 1 wherein:

said pestle is elongated and formed with a cylindrical center body defining said barrel; and said peripheral skirt is of cylindrical configuration and formed for telescopically receiving said barrel with said sealing lip in frictional, gripping engagement with said center body.

3. The apparatus of claim 2 wherein:

said pestle terminates at the respective longitudinal ends thereof in hemispherically shaped ends; and said cap includes a closed end formed with a concave inner wall configured for complemental engagement with one of said ends of said pestle.

4. The apparatus of claim 1 wherein:

said skirt is configured to cooperate with said barrel to define an annular flow passageway for flow of said mercury.

5. The apparatus of claim 1 wherein:

said pestle and cap are formed of plastic.

6. A dental amalgam storage capsule device as set forth in claim 1 that includes:

mercury material in said compartment.

7. A dental amalgam storage capsule device as set forth in claim 1 wherein:

said skirt is cylindrically shaped and said lip is in the form of a radially in-turned flange.

8. A storage capsule apparatus for storing a liquid component of a dental amalgam therein and being disposed in an outer capsule defining an internal mixing chamber and storing a second component of said dental amalgam in said chamber, said apparatus comprising:

an elongated pestle including a barrel defining a peripheral sealing wall; and a cap storing said liquid component therein and formed with a laterally flexible, resilient peripheral skirt terminating in an open end configured with an inwardly projecting sealing lip for slidably, flexibly and sealingly engaging said peripheral sealing wall to trap said liquid component in said cap, said lip being responsive to a predetermined axial force being applied to said pestle to force said pestle a predetermined distance into said cap to contact said liquid component and raise the hydraulic pressure thereof sufficiently to cause said sealing lip to separate from said sealing wall to release a predetermined quantity of said liquid component.

9. The apparatus of claim 8 wherein:

said pestle is formed with a cylindrical center body defining said barrel; and said peripheral skirt is of cylindrical configuration and formed for telescopically receiving said cylindrical center body of said pestle with said sealing lip in frictional, gripping engagement with said sealing wall.

10. The apparatus of claim 8 wherein:

said liquid component comprises mercury; and said other component comprises alloy powder.

11. The apparatus of claim 8 wherein:

said pestle terminates at the respective longitudinal ends thereof in hemispherically shaped ends; and said cap is formed at its closed end with a concave inner wall configured for complemental engagement with said ends of said pestle.

12. The apparatus of claim 8 wherein:

said lip is configured to cooperate with said sealing wall to, upon application of said predetermined axial force, define an annular flow passageway for flow of said liquid component.

13. The apparatus of claim 8 wherein:

said pestle and cap are formed of plastic.

14. The apparatus of claim 8 wherein:

said outer capsule comprises a pair of threadedly engageable end caps releasably engageable with one another to define said internal mixing chamber.

15. A method of storing and dispensing a liquid mercury component, including the following steps:

selecting an inner capsule assembly of the type having an elongated pestle defining a longitudinal axis and configured with an elongated barrel defining a peripheral sealing wall of a predetermined configuration;

a cap forming a cavity and including a flexible, resilient peripheral skirt terminating in an open end defined by an inwardly projecting resilient sealing lip configured to sealingly and slidably engage said peripheral sealing wall;

inserting a predetermined charge of said liquid mercury component in said cap; and inserting one extremity of said pestle into said open end to engage said sealing wall with said sealing lip to seal said mercury component in said compartment; and dispensing said mercury component by driving said pestle telescopically into said compartment to cause said pestle to engage said charge of liquid mercury component and decrease the volume of said cavity to raise the hydraulic pressure on said liquid sufficiently to force it against said skirt to flex said skirt away from said sealing wall sufficient to dispense a selected portion of said charge of liquid.

16. The method of claim 15 further including the following steps:

selecting an outer capsule including an inner wall and defining an interior mixing chamber;

dispensing a predetermined quantity of a powder component in said outer capsule;

after inserting said pestle into said cap, placing said pestle and cap in said interior mixing chamber; and sealing said outer capsule.

17. The method of claim 16 further including, after sealing said outer capsule, the step of:

subjecting said outer capsule to a vibratory movement to vibrate said outer capsule back and forth to drive said inner capsule assembly in its axial direction to repeatedly contact the opposite inner walls of said outer capsule to cause said cap to engage said inner wall to be rapidly decelerated so the momentum of said pestle will drive it further into said cavity against said liquid mercury component to apply sufficient pressure thereto to force said skirt radially outwardly to lift said sealing lip off said peripheral wall of said pestle to provide for ejection of a measure of said liquid component into said mixing chamber to mix with said liquid mercury component stored therein.

18. The method of claim 15 wherein:

said step of inserting said pestle into said cap includes placing said cap in a partial vacuum;

registering one extremity of said pestle in sealing engagement with said sealing lip; and subjecting said cap and pestle to an increased pressure to create a pressure differential across said pestle to drive said pestle into said cap.

19. A dental amalgam storage capsule device as set forth in claim 15 wherein:

said step of dispensing said mercury includes driving said pestle incremental distances into said compartment to initially raise said hydraulic pressure to incrementally release measured portions of said liquid mercury component.

20. A dental amalgam storage capsule device for storing mercury and metered release thereof and comprising:

an elongated pestle formed with a barrel of a predetermined cross-section to define an elongated peripheral sealing wall; and a cap formed with a storage compartment and configured with a resilient peripheral skirt slidably received over said barrel, said skirt configured to slidingly and sealingly engage said sealing wall;

a charge of mercury material in said compartment; and said skirt having sufficient resiliency to normally seal against said sealing surface against leakage of said mercury and operative upon said pestle being pressed into said compartment to contact and push against said mercury to raise the hydraulic pressure of said mercury to sealingly separate from said wall sufficient for flow of at least some mercury past said sealing lip.

21. A dental amalgam storage capsule device as set forth in claim 20 that includes:

mercury material in said compartment.

22. A dental amalgam storage capsule device for storing mercury for metered release thereof and comprising:

an elongated pestle formed with a barrel of a predetermined cross-section to define an elongated peripheral sealing wall; and a cap formed with a storage compartment and configured with a peripheral skirt slidably received over said barrel, said skirt terminating in a resilient sealing lip configured to slidingly and sealingly engage said sealing wall and having sufficient resiliency to normally seal against leakage of said mercury and operative upon mercury stored in said compartment being pressed against said sealing lip with a predetermined pressure to sealingly separate from said wall for flow of at least some mercury past said sealing lip.

23. A dental amalgam storage capsule device as set forth in claim 22 wherein:

said skirt is formed with inwardly turned sealing lips to sealingly engage said sealing wall.

24. A mixing capsule comprising:

a cap formed with a storage compartment and an axially elongated skirt element formed with an open end;

an elongated pestle having one extremity received in said open end and formed with a barrel element constructed to be complementally received in frictional sliding and sealing engagement with said skirt element;

mercury material received in said compartment; and one of said elements having sufficient resiliency to, upon said pestle being driven into said compartment to contact said mercury and raise the hydraulic pressure thereof to a predetermined pressure, flex laterally to create an opening between said skirt element and barrel element for escape of at least a portion of said mercury.

25. A storage capsule apparatus for storing a liquid component of a dental amalgam therein and being disposed in an outer capsule defining an internal mixing chamber and storing a second component of said dental amalgam in said chamber, said apparatus comprising:

an elongated pestle including a barrel defining a peripheral sealing wall; and a cap storing said liquid component therein and formed with a laterally flexible, resilient peripheral skirt terminating in an open end configured with a sealing lip for slidably, flexibly and sealing engaging said peripheral sealing wall to cooperate in trapping said liquid component in said cap, said lip being flexible laterally under a predetermined force to separate from said sealing wall to create a space between said lip and said wall.

* * * * *